United States Patent [19]

Umemoto et al.

[11] Patent Number: 4,542,243
[45] Date of Patent: Sep. 17, 1985

[54] PROCESS FOR PRODUCING 3-PHENOXYBENZYL 2-(4-ALKOXYPHENYL)-2-METHYLPROPYL ETHERS

[75] Inventors: Mitsumasa Umemoto; Tamotsu Asano; Teruyuki Nagata, all of Fukuoka; Satoshi Numata, Kanagawa, all of Japan

[73] Assignee: Mitsui Toatsu Chemicals, Inc., Tokyo, Japan

[21] Appl. No.: 540,017

[22] Filed: Oct. 7, 1983

[30] Foreign Application Priority Data

Oct. 19, 1982 [JP] Japan .................................. 57-182200
Nov. 12, 1982 [JP] Japan .................................. 57-197638

[51] Int. Cl.$^4$ ...................... C07C 41/24; C07C 41/16; C07C 43/267
[52] U.S. Cl. .................................. 568/636; 568/628; 568/637; 568/655; 568/656
[58] Field of Search ............... 568/628, 655, 637, 636, 568/638, 656

[56] References Cited

U.S. PATENT DOCUMENTS 4,397,864  8/1983  Nakatani et al. .................... 424/282

FOREIGN PATENT DOCUMENTS 2085006  4/1982  United Kingdom ................. 568/637

OTHER PUBLICATIONS

Augustine, Catalytic Hydrogenation-Techniques and Applications in Organic Synthesis (1974) 144–147.
Ruchardt, C., "Wanderungsverhaltnisse substituierter Phenylreste by ther Decarbonylierung von β-Aryl-isovaleraldehyden", Chemische Berichte, 94, No. 10, pp. 2609–2623 (1961).

Primary Examiner—Bernard Helfin
Attorney, Agent, or Firm—Browdy and Neimark

[57] ABSTRACT

The present invention relates to a process for producing 3-phenoxybenzyl 2-(4-alkoxyphenyl)-2-methylpropyl ethers having excellent insecticidal and acaricidal activities which are represented by formula (IV):

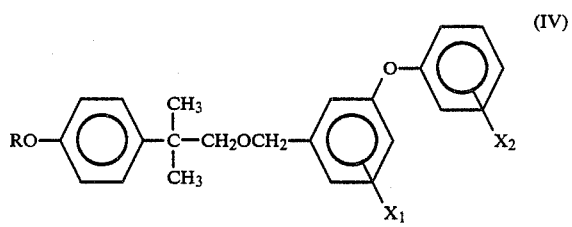

wherein R is a lower alkyl group and $X_1$ and $X_2$ are each a hydrogen or fluorine atom, which comprises reacting a 3-halogeno-4-alkoxyneophyl halide represented by the formula (I):

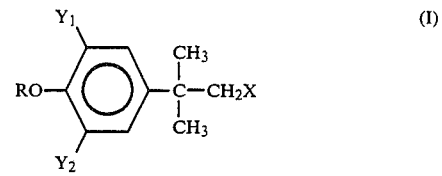

wherein $Y_1$ and $Y_2$ are each a hydrogen, chlorine or bromine atom, at least one of them being a chlorine or bromine atom, R has the same meaning as above and X is a halogen atom, with a 3-phenoxybenzyl alcohol represented by the formula (II):

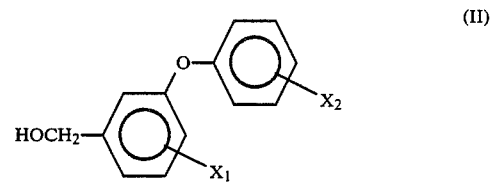

wherein $X_1$ and $X_2$ have the same meaning as above, in the presence of a base to obtain a 3-phenoxybenzyl 2-(4-alkoxy-3-halogenophenyl)-2-methylpropyl ether represented by the formula (III):

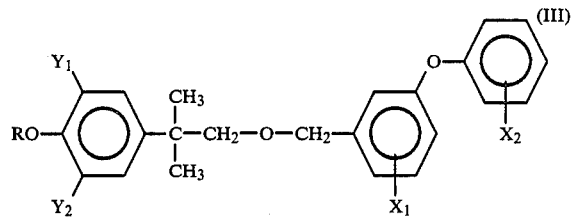

wherein $Y_1$, $Y_2$, R, $X_1$ and $X_2$ have the same meaning as above, and then subjecting the product to a hydrodehalogenation reaction, and relates to a process for producing a 3-halogeno-4-alkoxyneophyl halide represented by formula (I), which comprises reacting a 2-halogeno-1-alkoxybenzene represented by formula (V):

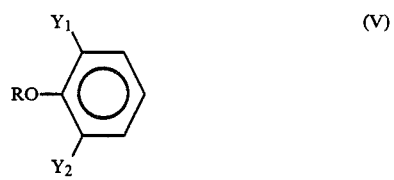

wherein $Y_1$ and $Y_2$ are each a hydrogen, chlorine or bromine atom, at least one of them being a chlorine or bromine atom, and R represents a lower alkyl group, with a methallyl halide in the presence of an acid catalyst at −20° to 50° C.

8 Claims, No Drawings

PROCESS FOR PRODUCING 3-PHENOXYBENZYL 2-(4-ALKOXYPHENYL)-2-METHYLPROPYL ETHERS

DETAILED DESCRIPTION OF THE INVENTION

The present invention relates to a process for producing 3-phenoxybenzyl 2-(4-alkoxyphenyl)-2-methylpropyl ethers represented by the formula (IV):

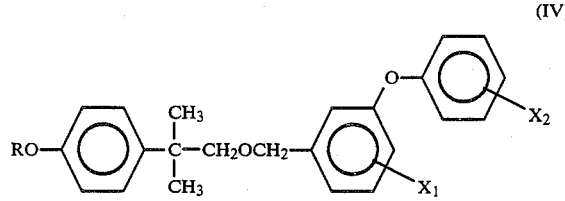

(IV)

wherein R is a lower alkyl group and $X_1$ and $X_2$ are each a hydrogen or fluorine atom.

More particularly, the invention relates to a process for producing a compound of the above formula (IV) by reacting a 3-halogeno-4-alkoxyneophyl halide represented by the formula (I):

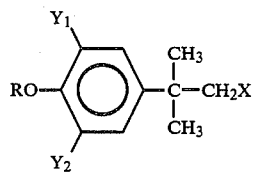

(I)

wherein $Y_1$ and $Y_2$ are each a hydrogen, chlorine or bromine atom, at least one of them being a chlorine or bromine atom, R is a lower alkyl group and X is a halogen atom, with a 3-phenoxybenzyl alcohol represented by the formula (II):

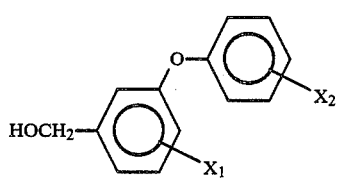

(II)

wherein $X_1$ and $X_2$ have the same meaning as above, in the presence of a base to obtain a 3-phenoxybenzyl 2-(4-alkoxy-3-halogenophenyl)-2-methylpropyl ether represented by the formula (III):

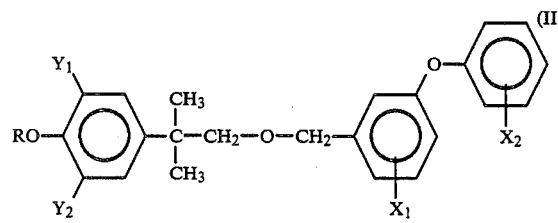

(III)

wherein $Y_1$, $Y_2$, R, $X_1$ and $X_2$ have the same meaning as above, and then subjecting the product to a hydrogenation reaction to remove the chlorine or bromine atom.

The present invention provides also a process for producing the compound of formula (I) used as the starting material for the compound of formula (III).

Recently, it has been found that some of 3-phenoxybenzyl ether derivatives including the compounds of the above formula (IV) have quite excellent insecticidal and acaricidal activities, excellent fast-acting property and residual activity but only an insignificant toxicity to not only men and animals but also fish, and excellent insectifuges comprising these compounds have been proposed.

Japanese Patent Laid-Open No. 154427/81 discloses 3-phenoxybenzyl ether derivatives of formula (VI):

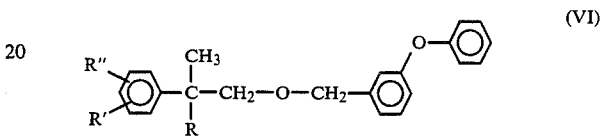

(VI)

wherein R is a methyl or ethyl group, R' is a hydrogen or halogen atom or a lower alkyl group and R" is a halogen atom or a lower alkyl group.

Japanese Patent Laid-Open Nos. 72928/82 and 64632/82 disclose compounds of the above formula (VI) wherein R' or R" is a halogen atom, a lower alkyl group or a lower alkoxyl group, or wherein the respective benzene nuclei of the 3-phenoxybenzyl group may be substituted with a halogen atom or the like.

The inventors have found that among the compounds disclosed in the above-mentioned patent publications, those of formula (VI) wherein either R' or R" is a lower alkoxyl group in position 4 and R is a methyl group, i.e., 3-phenoxybenzyl ether compounds having a neophyl group substituted with a lower alkoxyl group only in position 4 have a particularly high insecticidal activity. The inventors have also found that if the benzene nucleus of the neophyl group has a substituent such as a halogen atom or an alkyl group, the excellent effect of the compounds is reduced slightly.

After intensive investigations of processes for producing the compounds of the general formula (IV) which do not have any halogen atom nor alkyl group on the benzene nucleus of the neophyl group but which have only an alkoxyl group in position 4 of the benzene nucleus, the inventors have attained to the process of the present invention.

The specifications of the above-mentioned Japanese Patent Laid-Open No. 154427/81 etc. disclose processes for producing the compounds including the compounds of formula (IV). In these processes, these compounds are produced by reacting a compound of formula (VII):

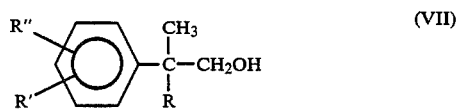

(VII)

wherein R, R' and R" have the same meaning as above, or its salt with a 3-phenoxybenzyl halide or an alcohol or, alternatively, by reacting a compound of formula (VIII):

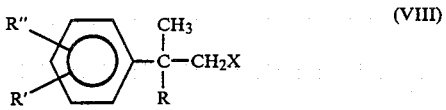

(VIII)

wherein X is a halogen atom and R, R' and R" have the same meaning as above, with a 3-phenoxybenzyl alcohol. The above-mentioned specifications disclose also processes for producing compounds of formulae (VII) and (VIII). However, a long reaction path is required in the process for synthesizing a compound of formula (VII). This process is industrially disadvantageous when a compound of formula (VII) is used as a starting material for a compound of formula (IV) (intended product of the present invention).

For the production of a compound of formula (VIII), for example, the following process is disclosed:

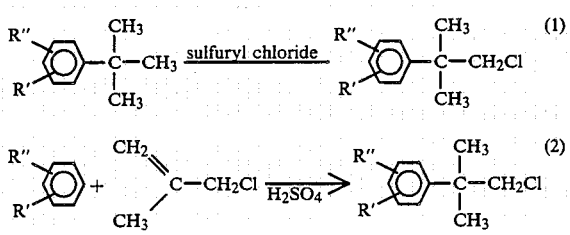

However, when either R' or R" is a lower alkoxyl group in position 4, a nuclear chlorination reaction proceeds preferentially in the above-mentioned process (1) to make it substantially difficult to obtain the intended 4-alkoxyneophyl chloride. In the above-mentioned process (2), the alkylation in a position ortho to the alkoxyl group proceeds preferentially, so that an o-isomer is by-produced in a large amount and the efficient separation of the isomers becomes difficult. Consequently, a highly pure 4-alkoxyneophyl chloride is obtained in a quite poor yield. In addition, the resulting 4-alkoxyneophyl chloride is an unstable compound and, therefore, the storage and handling of this product on an industrial scale are difficult.

Thus, it is disadvantageous to produce an intended compound of formula (IV) on an industrial scale by reacting a 4-alkoxyneophyl chloride with a 3-phenoxybenzyl alcohol.

The inventors have completed an industrial process for producing 3-phenoxybenzyl 2-(4-alkoxyphenyl)-2-methylpropyl ethers at a low cost on the basis of these findings. According to the process of the present invention, a starting compound of formula (I) is reacted with a compound of formula (II) in the presence of a base to obtain a compound of formula (III) and then the halogen atom on the benzene nucleus of the neophyl group is removed by a hydro-dehalogenation reaction to obtain an intended product of formula (IV).

In the production of the compound of formula (IV) at a low cost on an industrial scale according to the process of the present invention, it is necessary that the starting compound of formula (I) is obtained in a high yield. The inventors have found that the 3-halogeno-4-alkoxyneophyl halides of formula (I) can be obtained in a high yield by reacting a 2-halogeno-1-alkoxybenzene of formula (V):

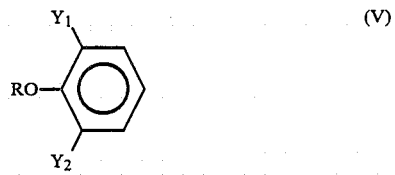

wherein $Y_1$ and $Y_2$ are each a hydrogen, chlorine or bromine atom, at least one of them being a chlorine or bromine atom, and R is a lower alkyl group, with a methallyl halide in the presence of an acid catalyst.

The inventors have found that even when $Y_1$ and $Y_2$ in the compound of formula (V) are chlorine and hydrogen, respectively, namely even when the compound is alkoxymonochlorobenzene, the resulting product comprised mainly a p-isomer obtained by preferentially introducing the methallyl halide into position 4 to the alkoxy group, while an o-isomer obtained by introducing the halide preferentially into position 6 to the alkoxy group is hardly formed.

The starting compound of formula (V) is available at a low cost on an industrial scale. For example, when the compound of formula (I) is o-chlorophenetole, this compound can be obtained from a starting compound obtained by an ordinary method such as ethylation of o-chlorophenol with an alkylating agent or alcoholysis of o-dichloro-benzene.

As the compound of the above formula (V) used as the starting material in the present invention, there may be mentioned, for example, 2-chloro-1-methoxybenzene, 2,6-dichloro-1-methoxybenzene, 2-bromo-1-methoxybenzene, 2,6-dibromo-1-methoxybenzene, 2-chloro-1-ethoxybenzene, 2,6-dichloro-1-ethoxybenzene, 2-bromo-1-ethoxybenzene, 2-chloro-1-propoxybenzene or 2-bromo-1-propoxybenzene. These compounds are reacted with methallyl chloride or methallyl bromide as will be shown below to obtain a compound of formula (I), which is isolated and purified for use as the starting material for the compound of formula (III) according to the present invention and also as an intermediate in the production of various organic compounds.

In the production of the 3-halogeno-4-alkoxy-neophyl halide of formula (I) according to the present invention, 0.5 to 10 mol, preferably 1 to 5 mol, of the methallyl halide is used per mol of the 2-halogeno-1-alkoxybenzene. When the proportion of them is not within this range, the reaction velocity is reduced and the by-product formation is accelerated, resulting in reducing the yield of the intended product.

The process of the present invention may be carried out in the absence of any solvent or in a solvent generally used for the Friedel-Crafts reaction, such as nitromethane, acetonitrile or carbon disulfide.

In the process of the present invention, the reaction is carried out in the presence of an acid catalyst. As the acid catalyst, there may be mentioned, for example, concentrated sulfuric acid, methanesulfonic acid, a strongly acidic ion exchange resin such as Amberlyst or Nafion, trifluoromethanesulfonic acid or hydrofluoric acid. Among these catalysts, trifluoromethanesulfonic acid is most preferred. However, concentrated sulfuric acid is one of preferred acid catalysts from the industrial viewpoint.

The acid catalyst is used in an amount of 0.1 to 2.0 mol, preferably 0.5 to 1.2 mol, per mol of the methallyl halide. If the proportion of them is not within this range, the reaction velocity is reduced or the by-products are formed in a large amount to reduce the yield.

The reaction temperature is −20° to 50° C., preferably 0° to 30° C. It is preferred to add the catalyst and the methallyl halide dropwise simultaneously to the compound of formula (V) to effect the reaction. When the methallyl halide is contacted with the acid catalyst for a long time, it is inclined to be deteriorated to form a polymer or the like. When the reaction temperature or the manner of the charging of the starting materials is different from that described above, the reaction velocity is reduced or the by-products are formed in a large amount. Generally, the catalyst and the methallyl halide are added dropwise simultaneously in 0.5 to 2 h and then the reaction mixture is kept for additional 2 to 6 h after completion of the addition to complete the reaction.

The thus obtained compound of formula (I) is substantially free of the o-isomer or the like and, therefore, its purification is generally unnecessary. Even when the purification is effected, the operation is easy, since it is a stable compound unlike the 4-alkoxyneophyl halide. In the subsequent etherification reaction, the ether can be obtained in a high yield.

The compound of formula (III) according to the present invention may be obtained by, for example, a process disclosed in the above-mentioned patent specification wherein a compound of formula (VIII) is reacted with a 3-phenoxybenzyl alcohol in the presence of a base such as an aqueous sodium hydroxide solution in a reaction solvent such as dimethyl sulfoxide to obtain a compound of formula (VI).

However, when the 3-halogeno-4-alkoxyneophyl halide of formula (I) wherein the benzene nucleus of the neophyl group is substituted with an alkoxyl group and an chlorine or bromine atom is reacted with the 3-phenoxybenzyl alcohol of formula (II) in dimethyl sulfoxide used as the reaction solvent in the process of the present invention, the reaction yield is relatively low. Further, it is to be noted that when a polar solvent containing sulfur atom such as dimethyl sulfoxide is used in the etherification reaction, by-products containing a sulfur atom formed in the course of the etherification reaction remain in a very small amount in the compound of formula (III) even after the purification by recrystallization. These by-products containing a sulfur atom act as catalyst poison in the subsequent step of the hydrodehalogenation carried out in the presence of a hydrogenation catalyst, whereby the yield of the intended compound of formula (IV) is reduced seriously.

Therefore, in the production of the compound of formula (III) by the etherification reaction of the compound of formula (I) with the compound of formula (II) according to the process of the present invention, it is preferred to carry out the reaction in the presence of an aprotic polar solvent containing no sulfur atom. As such a solvent, there may be mentioned, for example, 1,3-dimethyl-2-imidazolidinone, N-methyl-2-pyrrolidone, tetramethylurea, diglyme or hexamethylphosphoric triamide. Among them, 1,3-dimethyl-2-imidazolidinone is preferred, since a high yield can be obtained when it is used.

The amount of the solvent is 0.5 to 50 parts, preferably 2 to 20 parts, per part of 3-phenoxybenzyl alcohol. If the amount of the solvent is smaller, the reaction velocity is lowered seriously. If the amount of the solvent is larger, the reaction velocity is lowered and the productivity is reduced.

As the base used, there may be mentioned an alkali metal hydroxide such as sodium hydroxide, potassium hydroxide or lithium hydroxide; an alkaline earth metal hydroxide such as calcium hydroxide or magnesium hydroxide; an alkali metal hydride such as sodium hydride; an alkali metal alcoholate such as sodium methylate, potassium ethylate or potassium t-butoxide; an alkali metal oxide such as sodium oxide; an alkali metal carbonate such as potassium carbonate or sodium carbonate; sodium amide; triethylamine; or pyridine. The base is used in an amount of 0.5 to 3 mol, preferably 1 to 2 mol, per mol of the 3-phenoxybenzyl alcohol. If the amount of the base is smaller, the conversion becomes poor. If the amount of the base is larger, by-products are formed in a large amount to reduce the yield.

As the base, sodium hydroxide or potassium hydroxide is preferred. It is desirable to use the alkali in the form of solid, since the reaction is accelerated and the yield is improved when ordinary, granular or flaky alkali or, in some cases, finely pulverized alkali is used. The water content of the reaction system is up to 10%, preferably up to 3%, based on the solvent in the initial stage of the reaction. In some cases, it is effective to carry out an azeotropic dehydration with toluene or xylene in the course of the reaction.

A general embodiment of the etherification step according to the present invention is as follows: as for the proportion of the compound of formula (I) to the compound of formula (II), a 3-halogeno-4-alkoxyneophyl halide of formula (I) is used in an amount of 0.2 to 5 mol, preferably 0.4 to 2 mol, per mol of a 3-phenoxybenzyl alcohol of formula (II). If the proportion is not within this range, the reaction velocity is reduced and the formation of by-products is accelerated to reduce the yield.

Compounds of formulas (I) and (II), a base and a solvent are charged in a reaction vessel and heated to 50° C. to a boiling point, preferably 80° C. to a boiling point (when the boiling point is above 200° C., they are heated to 80° to 200° C.). The mixture is stirred at that temperature for 0.5 to 50 h, preferably 3 to 30 h. After cooling to room temperature, an insoluble inorganic salt is filtered out. The solvent is removed from the filtrate by vacuum distillation. The residue is washed with water and dried to obtain a 3-phenoxybenzyl 2-(4-alkoxy-3-halogenophenyl)-2-methylpropyl ether or 3-phenoxybenzyl 2-(4-alkoxy-3,5-dihalogenophenyl)-2-methylpropyl ether of formula (III). The product is purified by vacuum distillation or column chromatography and, if necessary, recrystallized.

As the compound of formula (III), there may be used those having a monohalogenated benzene nucleus in the neophyl group, such as 3-phenoxybenzyl 2-(3-chloro-4-alkoxyphenyl)-2-methylpropyl ether, 3-phenoxybenzyl 2-(3-bromo-4-alkoxyphenyl)-2-methylpropyl ether or 3-phenoxy-4-fluorobenzyl 2-(3-chloro-4-alkoxyphenyl)-2-methylpropyl ether; or those having a dihalogenated benzene nucleus in the neophyl group, such as 3-phenoxybenzyl 2-(3,5-dichloro-4-alkoxyphenyl)-2-methylpropyl ether. An intended compound of formula (III) may be obtained by suitably selecting the compounds of formulas (I) and (II). In the process of the present invention, the monochloro-substituted compound is preferred for subsequently hydrodehalogenating the compound of formula (III) to obtain the intended product of formula (IV). Among the compounds of formula (I), the 3-chloro-4-alkoxyneophyl chloride is, therefore, particularly preferred.

The thus obtained compound of formula (III) is then hydrodehalogenated in a catalytic hydrogenation step to obtain a corresponding compound of formula (IV).

In the process of the present invention, the compound of formula (IV) may be obtained from the compound of formula (III) by, for example, a catalytic hydrogenation method, a hydrogenation method with a reducing agent such as lithium aluminum hydride, or a dehalogenation method with a metal in an aprotic polar solvent. Among them, the hydrogenation method, particularly the catalytic hydrogenation method is industrially most advantageous. According to the catalytic hydrogenation method, the compound of formula (IV) is obtained by, for example, as follows:

A compound of formula (III) is reacted with hydrogen in the presence or absence of a base and a solvent in the presence of a catalyst at a given temperature under atmospheric or elevated pressure. Then, a compound of formula (IV) is separated from the reaction mixture by a proper method.

As the base, there may be mentioned an alkali metal hydroxide, carbonate, acetate or alcoholate such as potassium hydroxide, sodium hydroxide, potassium carbonate, sodium carbonate, sodium acetate or sodium methylate; an alkaline earth metal hydroxide such as calcium hydroxide; or an aliphatic, aromatic or heterocyclic base such as triethylamine, ethylenediamine, diethylaniline, pyridine or 1,5-diazabicyclo[5.4.0]undec-5-ene (DBU). Among them, the alkali metal hydroxide is preferred. Particularly, sodium hydroxide is advantageous from the economical viewpoint. The amount of the base may be determined over a wide range. Generally, 0 to 10 mol, preferably 1 to 6 mol of the base is used per mol of the compound of formula (III).

When the reaction is carried out in a reaction solvent, there may be used, in addition to water, an alcohol such as methanol, a polyhydric alcohol such as ethylene glycol; acetic acid; an acetate; or another organic solvent. The organic solvent may be used in the form of a mixture with water. Particularly a mixture of water and methanol is preferred. The amount of the reaction solvent may be determined in the range of 0 to 100 parts by volume per part by volume of the starting compound of formula (III). In view of the reaction velocity, volumetric efficiency of the reaction vessel, etc., an amount of 2 to 10 parts by volume is desirable.

As the catalyst, there may be used a nickel catalyst such as Raney nickel; palladium catalyst such as palladium carbon; or platinum catalyst. Palladium carbon is particularly advantageous. The amount of the catalyst is 0.1 to 20 wt. %, preferably 2 to 7 wt. %, based on the compound of formula (III).

The hydrodehalogenation reaction according to the present invention may be carried out under atmospheric pressure. However, it is preferred to effect the reaction under elevated pressure of particularly 5 to 60 kg/cm².

The reaction can be carried out at a temperature over a wide range. The reaction temperature is generally 50° to 220° C., preferably 80° to 150° C.

Thus, by the hydrodehalogenation reaction according to the present invention, only the chlorine or bromine atom on the benzene nucleus of the neophyl group is removed. Even when the benzene nucleus is substituted with two halogen atoms, the chlorine or bromine atoms can be removed easily substantially without removing the fluorine atom on the benzene nucleus of the 3-phenoxybenzyl group. The intended product of formula (IV) can thus be obtained.

As the compound of formula (IV) obtained by removing the chlorine or bromine atom from the compound of formula (III), there may be mentioned, for example, 3-phenoxybenzyl 2-(4-methoxyphenyl)-2-methylpropyl ether, 3-phenoxy-4-fluorobenzyl 2-(4-methoxyphenyl)-2-methylpropyl ether, 3-(4-fluorophenoxy)benzyl 2-(4-methoxyphenyl)-2-methylpropyl ether, 3-(4-fluorophenoxy)-4-fluorobenzyl 2-(4-methoxyphenyl)-2-methylpropyl ether, 3-phenoxybenzyl 2-(4-ethoxyphenyl)-2-methylpropyl ether, 3-phenoxy-4-fluorobenzyl 2-(4-ethoxyphenyl)-2-methylpropyl ether, 3-(4-fluorophenoxy)benzyl 2-(4-ethoxyphenyl)-2-methylpropyl ether, 3-(4-fluorophenoxy)-4-fluorobenzyl 2-(4-ethoxyphenyl)-2-methylpropyl ether, 3-phenoxy-6-fluorobenzyl 2-(4-ethoxyphenyl)-2-methylpropyl ether, 3-(2-fluorophenoxy)benzyl 2-(4-ethoxyphenyl)-2-methylpropyl ether, 3-phenoxybenzyl 2-[4-(isopropoxy)phenyl]-2-methylpropyl ether, 3-phenoxy-4-fluorobenzyl 2-[4-(isopropoxy)phenyl]-2-methylpropyl ether, 3-phenoxybenzyl 2-[4-(1-methylpropoxy)phenyl]-2-methylpropyl ether, 3-phenoxybenzyl 2-[4-(n-butoxy)phenyl]-2-methylpropyl ether, 3-phenoxybenzyl 2-[4-(t-butoxy)phenyl]-2-methylpropyl ether or 3-phenoxybenzyl 2-[4-(n-pentyloxy)phenyl]-2-methylpropyl ether.

The following examples will further illustrate the present invention.

EXAMPLE 1

Synthesis of 2-(3-chloro-4-ethoxyphenyl)-2-methylpropyl chloride (Synthesis of 3-chloro-4-ethoxyneophyl chloride)

208.6 g (1.33 mol) of o-chlorophenetole was charged in a 500 ml four-neck flask. 39.2 g (0.40 mol) of 98% sulfuric acid and 90.6 g (1.00 mol) of methallyl chloride were added dropwise simultaneously through two dropping funnels at 10° C. over 2 h. Then, the mixture was stirred at the same temperature for additional 2 h.

The reaction solution was poured into about 0.5 l of water. The mixture was shaken well in a separatory funnel to divide the same into a lower oil layer and an aqueous layer. The oil layer was washed with 200 g of a 3% aqueous sodium hydroxide solution and then 200 g of water three times and finally dehydrated under reduced pressure to obtain 287.8 g of crude 2-(3-chloro-4-ethoxyphenyl)-2-methylpropyl chloride.

The crude product was analyzed according to gas chromatography to reveal that it comprised 96.5% of 2-(3-chloro-4-ethoxyphenyl)-2-methylpropyl chloride and 3.5% of 2-(3-chloro-2-ethoxyphenyl)-2-methylpropyl chloride.

The crude product was purified by vacuum distillation to obtain 167.4 g of the intended pure product (fraction of 127° to 135° C./1.5 mmHg).

Purity (gas chromatography; area %): 96.3%.

Yield: 67.7% based on methallyl chloride.

Elementary analysis as $C_{12}H_{16}Cl_2O$: Calculated: C: 58.31, H: 6.53, Cl: 28.69. Found: C: 58.11, H: 6.41, Cl: 28.72.

NMR spectrum $\delta CDCl_3$

-continued

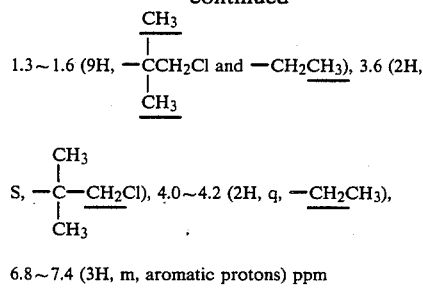

6.8~7.4 (3H, m, aromatic protons) ppm

EXAMPLE 2

The reaction and the after-treatment were effected in the same manner as in Example 1 except that 39.2 g of 98% sulfuric acid was replaced with 11.6 g of trifluoromethanesulfonic acid. 293.8 g of crude 2-(3-chloro-4-ethoxyphenyl)-2-methylpropyl chloride was obtained.

The crude product was analyzed according to gas chromatography to reveal that it comprised 96% of intended 2-(3-chloro-4-ethoxyphenyl)-2-methylpropyl chloride and 4% of 2-(3-chloro-2-ethoxyphenyl)-2-methylpropyl chloride (isomer).

The crude product was distilled under reduced pressure to recover 67.7 g of unreacted o-chlorophenetole and to obtain 175.1 g of the intended pure compound (131 to 135° C./5 mmHg).

Purity (gas chromatography: area %): 93.6%
Yield: 70.9% (based on methallyl chloride)

REFERENTIAL EXAMPLE 2-(4-Ethoxyphenyl)-2-methylpropyl chloride (p-ethoxyneophyl chloride) was synthesized by the following process based on the known processes as described in Japanese Patent Laid-Open No. 72928/82 or the like:

120 g of 98% sulfuric acid was charged in a 500 ml four-neck flask. 200 g of phenetole was added dropwise thereto while the temperature was kept at 45° C. A mixed solution of 90 g of methallyl chloride and 165 g of phenetole was added dropwise thereto over 10 h while the temperature was kept at 0° to 10° C. The mixture was kept at 25° C. for 15 h and then poured into ice/water. An organic layer was separated out, washed thoroughly with a dilute aqueous sodium hydroxide solution and then water and dried over anhydrous sodium sulfate to obtain 451.2 g of crude 2-(2-ethoxyphenyl)-2-methylpropyl chloride. The crude product was analyzed according to gas chromatography to reveal that it comprised 22% of 2-(4-ethoxyphenyl)-2-methylpropyl chloride and 78% of 2-(2-ethoxyphenyl)-2-methylpropyl chloride (isomer).

EXAMPLE 3

Synthesis of 3-phenoxybenzyl 2-(3-chloro-4-ethoxyphenyl)-2-methylpropyl ether 3 l (3,156 g) of 1,3-dimethyl-2-imidazolidinone (hereinafter referred to as DMI), 618.0 g (2.50 mol) of purified 2-(3-chloro-4-ethoxyphenyl)-2-methylpropyl chloride obtained in the same manner as in Example 1, 1,251.0 g (6.25 mol) of m-phenoxybenzyl alcohol (a product of Ethyl Corp.) and 280.0 g (5.00 mol) of potassium hydroxide in the form of flakes were charged in a 5 l four-neck flask and stirred at 120° C. under nitrogen stream for 15 h to complete the reaction.

The reaction mass was cooled to room temperature. An insoluble matter was filtered out under reduced pressure. The filtrate was washed with 300 ml (320 g) of DMI to obtain 5,215 g of a mother wash solution. 3,274 g of DMI was recovered from this solution by vacuum distillation. 1,845 g of a residue containing an inorganic matter was obtained.

It was confirmed that the residue contained 3-phenoxybenzyl 2-(3-chloro-4-hydroxyphenyl)-2-methylpropyl ether (deethylated product) by-produced in the course of the reaction. The product had the following physical properties:

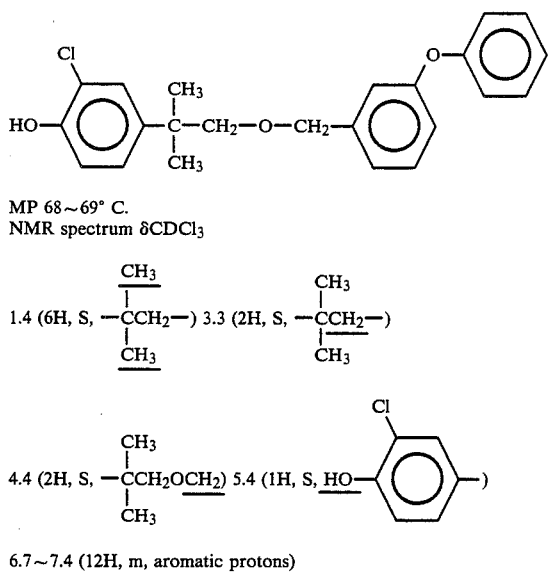

MP 68~69° C.
NMR spectrum δCDCl₃

6.7~7.4 (12H, m, aromatic protons)

To recover the deethylated compound in the form of an ethylated compound, the residue was charged in a 5 l four-neck flask together with 3,000 ml of water. 38.5 g (0.25 mol) of diethyl sulfate was added dropwise thereto at 50° C. in 1 h. The mixture was stirred at that temperature for 1 h. The temperature was elevated to 90° C. and stirring was effected at that temperature for 2 h to decompose excessive diethyl sulfate. The reaction mass was cooled to 50° C. and adjusted to pH 3 to 4 with 30 g of concentrated hydrochloric acid. The mixture was left to stand. A resulting lower oily layer was separated and washed with 3 l of water at 50° C. The washing was repeated further twice. A resulting oily product containing water was dehydrated by means of an evaporator under reduced pressure to obtain 1,774 g of a residue.

The residue was distilled under reduced pressure in a Smith's thin film evaporator to remove low boiling unreacted starting materials (210° C./0.1 mmHg). The residue was thus divided into 990 g of a low boiling fraction and 770 g of a high boiling fraction.

A mixed solution of 770 g of the high boiling fraction and 1,540 ml of methanol was cooled to −10° C. and stirred at that temperature for 2 h to form crystals. The crystals were filtered and dried.

According to the gas chromatographic analysis by the internal standard method, the product comprised 96.3% of 3-phenoxybenzyl 2-(3-chloro-4-ethoxyphenyl)-2-methylpropyl ether and 0.6% of 3-phenoxybenzyl 2-(3-chloro-4-ethoxyphenyl)-1,1-dimethylethyl ether (isomer).

Yield of the crystals: 869.5 g (81.5%).

The crystals had the following solidifying point, elementary analysis values and NMR spectral data:

Solidifying point: 42.2° C.
Elementary analysis as $C_{25}H_{27}ClO_3$

| | C | H | Cl |
|---|---|---|---|
| Calculated: | 73.07 | 6.62 | 8.63 |
| Found: | 73.25 | 6.55 | 8.33 |

NMR spectrum $\delta CDCl_3$
1.25 (6H. s), 1.2 (3H. t), 3.36 (2H. s), 3.92 (2H. q), 4.2 (2H. s), 6.6~7.4 (12H. m) ppm

EXAMPLE 4

Synthesis of 3-phenoxy-4-fluorobenzyl 2-(3-chloro-4-ethoxyphenyl)-2-methylpropyl ether 30 ml of DMI, 6.2 g (0.025 mol) of purified 2-(3-chloro-4-ethoxyphenyl)-2-methylpropyl chloride obtained in Example 1, 8.5 g (0.039 mol) of 3-phenoxy-4-fluorobenzyl alcohol and 2.2 g (0.039 mol) of potassium hydroxide in the form of flakes were charged in a 100 ml flask and stirred at 120° C. under nitrogen stream for 15 h to complete the reaction.

The reaction mass was cooled to room temperature and then poured into 200 ml of a 5% aqueous hydrochloric acid solution. A resulting oily product was extracted with 100 ml of benzene. The benzene extract was washed with 100 ml of water three times and dried over anhydrous Glauber salt. Benzene was distilled off under reduced pressure to obtain 13.8 g of an oily product. According to gas chromatographic analysis by the internal standard method, the product contained 62.4% of 3-phenoxy-4-fluorobenzyl 2-(3-chloro-4-ethoxyphenyl)-2-methylpropyl ether. Yield: 80.5%. The oily product was isolated and purified according to column chromatography using silica gel to obtain 7.3 g of the pure product (oily product).

The oily product had the following refractive index, elementary analysis values and NMR spectral data:

$n_D^{20.0}$ 1.1576
Elementary analysis as $C_{25}H_{26}ClFO_3$

| | C | H | Cl | F |
|---|---|---|---|---|
| Calculated: | 70.01 | 6.11 | 8.26 | 4.43 |
| Found: | 70.12 | 6.00 | 8.58 | 4.21 |

NMR spectrum $\delta CDCl_3$
1.27 (6H. s), 1.42 (3H. t), 3.30 (2H. s), 4.05 (2H. q), 4.34 (2H. s), 6.6~7.4 (11H. m) ppm

EXAMPLE 5

Synthesis of 3-phenoxybenzyl 2-(3-bromo-4-ethoxyphenyl)-2-methylpropyl ether 30 ml of DMI, 7.3 g (0.025 mol) of 2-(3-bromo-4-ethoxyphenyl)-2-methylpropyl chloride obtained in the same manner as in Example 1 except that o-chlorophenetole was replaced with o-bromophenetole, 8.5 g (0.039 mol) of m-phenoxybenzyl alcohol and 2.2 g (0.039 mol) of flaky potassium hydroxide were charged in a 100 ml flask and stirred at 120° C. under nitrogen stream for 15 h to complete the reaction.

The reaction mass was cooled to room temperature and then poured into 200 ml of a 5% aqueous hydrochloric acid solution. A resulting oily product was extracted with 100 ml of benzene. The benzene extract was washed with 100 ml of water three times and then dried over anhydrous Glauber salt. Benzene was distilled off under reduced pressure to obtain 14.2 g of an oily product.

According to gas chromatographic analysis by the internal standard method, the product contained 58.3% of 3-phenoxybenzyl 2-(3-bromo-4-ethoxyphenyl)-2-methylpropyl ether. Yield: 72.7%. The oily product was isolated and purified according to column chromatography using silica gel to obtain 8.8 g of the pure product (oily product).

The oily product had the following elementary analysis values and NMR spectral data:

Elementary analysis as $C_{25}H_{27}BrO_3$

| | C | H | Br |
|---|---|---|---|
| Calculated: | 65.93 | 5.99 | 17.55 |
| Found: | 65.65 | 5.82 | 17.65 |

NMR spectrum $\delta CDCl_3$
1.26 (6H. s), 1.2 (3H. t), 3.35 (2H. s), 3.92 (2H. q), 4.4 (2H. s), 6.6~7.4 (12H. m) ppm

EXAMPLE 6

Synthesis of 3-phenoxybenzyl 2-(4-ethoxyphenyl)-2-methylpropyl ether 60.0 g (0.146 mol) of 3-phenoxybenzyl 2-(3-chloro-4-ethoxyphenyl)-2-methylpropyl ether, 7.5 g (0.188 mol) of flaky sodium hydroxide, 7.2 g of 5% palladium carbon (50% wet), 108 ml of methanol and 36 ml of water were charged in a 500 ml autoclave. The autoclave was closed tightly and purged with nitrogen. Then, hydrogen was introduced therein to attain a pressure of 8 kg/cm²G. The mixture was stirred at an internal temperature of 110° C. for 12 h while 8–10 kg/cm²G of hydrogen was supplemented to complete the reaction.

The reaction mixture was cooled to room temperature and the gas was released. 120 ml of benzene was charged in the autoclave to dissolve an oil layer. An insoluble matter was filtered out. After washing with 30 ml of benzene, a resulting mother wash solution was shaken well and then left to stand to obtain a benzene layer. The benzene layer was washed with 120 ml of water three times and then separated from water. Benzene was distilled off under reduced pressure to obtain an oily product. According to gas chromatographic analysis by the internal standard method, the product contained 98.5% of 3-phenoxybenzyl 2-(4-ethoxyphenyl)-2-methylpropyl ether and 0.5% of unreacted 3-phenoxybenzyl 2-(3-chloro-4-ethoxyphenyl)-2-methylpropyl ether. The amounts of 3-phenoxytoluene and 4-ethoxyneophyl alcohol formed by ether bond cleavage were each less than 0.2%.

Yield of the oily product: 53.6 g (96.0%)

The oily product had the following solidifying point, elementary analysis values and NMR spectral data:

Solidifying point: 31.2° C.
Elementary analysis as $C_{25}H_{28}O_3$:

| | C | H |
|---|---|---|
| Calculated: | 79.75 | 7.50 |
| Found: | 79.86 | 7.69 |

NMR spectrum $\delta CDCl_3$
1.25 (6H, s), 1.3 (3H, t), 3.35 (2H, s), 3.92 (2H, q), 4.2 (2H, s), 6.6~7.4 (13H, m) ppm

EXAMPLE 7

50.0 g (0.110 mol) of purified 3-phenoxybenzyl 2-(3-bromo-4-ethoxyphenyl)-2-methylpropyl ether obtained in the same manner as in Example 5, 4.8 g (0.121 mol) of flaky sodium hydroxide, 2.0 g of 5% palladium carbon (50% wet), 90 ml of methanol and 30 ml of water were charged in a 500 ml autoclave. The autoclave was closed tightly and purged with nitrogen. Then, hydrogen was introduced therein to attain a pressure of 10 kg/cm$^2$G. The mixture was stirred at an internal temperature of 80° C. for 12 h while 8–10 kg/cm$^2$G of hydrogen was supplemented to complete the reaction.

The reaction mixture was cooled to room temperature and the gas was released. 100 ml of benzene was charged in the autoclave to dissolve an oil. An insoluble matter was filtered out. After washing with 20 ml of benzene, a resulting mother wash solution was shaken well and then left to stand to obtain a benzene layer. The benzene layer was washed with 100 ml of water three times. Benzene was distilled off under reduced pressure to obtain an oily product. According to gas chromatographic analysis by the internal standard method, the oily product contained 98.5% of intended 3-phenoxybenzyl 2-(4-ethoxyphenyl)-2-methylpropyl ether and 0.3% of starting material 3-phenoxybenzyl 2-(3-bromo-4-ethoxyphenyl)-2-methylpropyl ether. The amounts of 3-phenoxytoluene and 4-ethoxyneophy alcohol formed by ether bond cleavage were each less than 0.2%.

Yield of the oily product: 41.2 g (yield: 98.0%)

The oily product had the following solidifying point, elementary analysis values and NMR spectral data:

| Solidifying point: 33.1° C. | | |
|---|---|---|
| Elementary analysis as C$_{25}$H$_{28}$O$_3$ | | |
| | C | H |
| Calculated: | 79.75 | 7.50 |
| Found: | 79.50 | 7.22 |
| NMR spectrum δCDCl$_3$ | | |
| 1.25 (6H, s), 1.3 (3H, t), 3.35 (2H, s), 3.92 | | |
| (2H, q), 4.2 (2H, s), 6.6~7.4 (13H, m) ppm | | |

EXAMPLE 8

Synthesis of 3-phenoxy-4-fluorobenzyl 2-(4-ethoxyphenyl)-2-methylpropyl ether:

50.0 g (0.117 mol) of purified 3-phenoxy-4-fluorobenzyl 2-(3-chloro-4-ethoxyphenyl)-2-methylpropyl ether obtained in the same manner as in Example 4, 5.6 g (0.140 mol) of flaky sodium hydroxide, 5 g of 5% palladium carbon (50% wet), 90 ml of methanol and 30 ml of water were charged in a 500 ml autoclave. The autoclave was closed tightly. After purging with nitrogen, hydrogen was introduced therein to attain a pressure of 10 kg/cm$^2$G. The mixture was stirred at an internal temperature of 100° C. for 15 h while 8 to 10 kg/cm$^2$G of hydrogen was supplemented to complete the reaction.

The reaction mixture was cooled to room temperature and the gas was released. 100 ml of benzene was charged in the autoclave to dissolve an oil. An insoluble matter was filtered out. After washing with 20 ml of benzene, a resulting mother wash solution was shaken well and then left to stand to obtain a benzene layer. The benzene layer was washed with 100 ml of water three times. Benzene was distilled off under reduced pressure to obtain an oily product. According to gas chromatographic analysis by the internal standard method, the oily product contained 97.2% of 3-phenoxy-4-fluorobenzyl 2-(4-ethoxyphenyl)-2-methylpropyl ether and 1.0% of starting material 3-phenoxy-4-fluorobenzyl 2-(3-chloro-4-ethoxyphenyl)-2-methylpropyl ether. The amounts of 3-phenoxytoluene and 4-ethoxyneophyl alcohol formed by ether bond cleavage were each less than 0.1%. The amount of 3-phenoxybenzyl 2-(4-ethoxyphenyl)-2-methylpropyl ether formed probably due to the replacement of fluorine atom with hydrogen atom was only less than 0.5%.

Yield of the oily product: 45.1 g (95.0%).

The oily product had the following solidifying point, elementary analysis values and NMR spectral data:

| n$_D^{20.0}$: 1.5635 | | | |
|---|---|---|---|
| Elementary analysis as C$_{25}$H$_{27}$FO$_3$ | | | |
| | C | H | F |
| Calculated: | 76.12 | 6.90 | 4.82 |
| Found: | 75.95 | 6.98 | 4.69 |
| NMR spectrum δCDCl$_3$ | | | |
| 1.28 (6H, s), 1.39 (3H, t), 3.29 (2H, s), | | | |
| 3.92 (2H, q), 4.32 (2H, s), 6.6~7.4 | | | |
| (12H, m) ppm | | | |

What is claimed is:

1. A process for producing 3-phenoxybenzyl 2-(4-alkoxyphenyl)-2-methylpropyl ethers represented by the formula (IV):

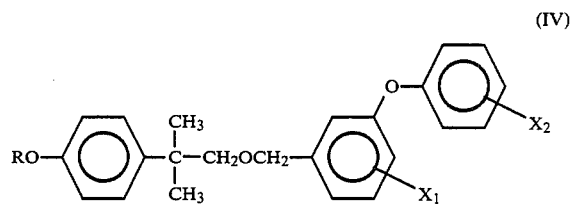
(IV)

wherein R is a lower alkyl group and X$_1$ and X$_2$ are each a hydrogen or fluorine atom, which comprises reacting a 2-halogeno-1-alkoxybenzene represented by formula (V):

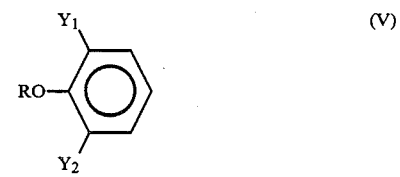
(V)

wherein Y$_1$ and Y$_2$ are each a hydrogen, chlorine or bromine atom, at least one of them being a chlorine or bromine atom, and R has the same meaning as above, with a methallyl halide in the presence of an acid catalyst at −20° to 50° C. to yield a 3-halogeno-4-alkoxyneophyl halide represented by the formula (I):

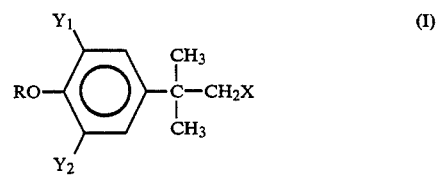
(I)

wherein Y$_1$, Y$_2$ and R have the same meaning as above and X is a halogen atom, then reacting said 3-halogeno-4-alkoxyneophyl halide represented by the formula (I) with a 3-phenoxygenzyl alcohol represented by the formula (II):

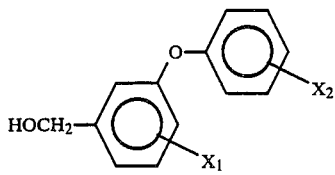

wherein $X_1$ and $X_2$ have the same meaning as above, in the presence of a base to yield a 3-phenoxybenzyl 2-(4-alkoxy-3-halogenophenyl)-2-methyl-propyl ether represented by the formula (III):

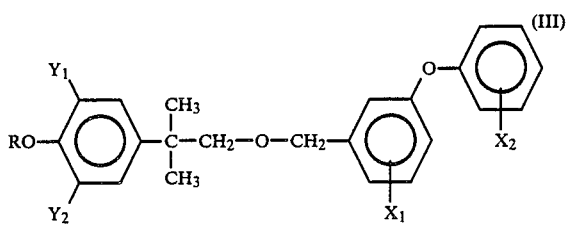

wherein $Y_1$, $Y_2$, R, $X_1$ and $X_2$ have the same meaning as above, and then subjecting the product to a hydrodehalogenation reaction.

2. A process according to claim 1 wherein one of $Y_1$ and $Y_2$ is a hydrogen atom and the other is a chlorine atom.

3. A process according to claim 1, wherein said step of reacting a 3-halogeno-4-alkoxyneophyl halide of formula (I) with a 3-phenoxybenzyl alcohol of formula (II) in the presence of a base takes place in an aprotic polar solvent containing no sulfur atom.

4. A process according to claim 3 wherein the aprotic polar solvent containing no sulfur atom is 1,3-dimethyl-2-imidazolidinone.

5. A process according to claim 1 wherein the hydrodehalogenation of the compound of formula (III) is effected by a catalytic hydrogenation carried out in the presence of a base and a catalyst.

6. A process according to claim 1, wherein the acid catalyst is trifluoromethanesulfonic acid.

7. A process according to claim 1 wherein the acid catalyst is concentrated sulfuric acid.

8. A process according to claim 1, wherein the acid catalyst and the methallyl halide are added simultaneously to the 2-halogeno-1-alkoxybenzene of formula (V).

* * * * *